US008365068B2

(12) United States Patent
Brandt et al.

(10) Patent No.: US 8,365,068 B2
(45) Date of Patent: Jan. 29, 2013

(54) SYSTEM AND USER INTERFACE FOR WORKFLOW AND TASK SCHEDULE CONFIGURATION (75) Inventors: Samuel I. Brandt, Malvern, PA (US); Jan DeHaan, Downington, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 254 days.

(21) Appl. No.: 12/629,075

(22) Filed: Dec. 2, 2009

(65) Prior Publication Data
US 2010/0131289 A1 May 27, 2010

Related U.S. Application Data (62) Division of application No. 10/212,556, filed on Aug. 5, 2002, now Pat. No. 7,653,873.

(60) Provisional application No. 60/316,603, filed on Aug. 31, 2001.

(51) Int. Cl.
*G06F 17/00* (2006.01)
*G06F 9/46* (2006.01)
*G06Q 10/00* (2006.01)

(52) U.S. Cl. ........ 715/234; 715/205; 715/255; 715/760; 705/1.1; 705/7.27; 718/100

(58) Field of Classification Search .......... 715/200–205, 715/207, 210, 234, 243, 255, 256, 273, 274, 715/277, 713, 746, 747, 760, 762; 718/100, 718/101, 102, 106; 705/1.1, 7.27
See application file for complete search history.

(56) References Cited

U.S. PATENT DOCUMENTS

| | | | |
|---|---|---|---|
| 5,721,913 A | 2/1998 | Ackroff et al. | |
| 5,745,901 A | 4/1998 | Entner et al. | |
| 5,758,095 A | 5/1998 | Albaum et al. | |
| 5,790,119 A | 8/1998 | Sklut et al. | |
| 5,799,297 A | 8/1998 | Goodridge et al. | |
| 5,826,239 A | 10/1998 | Du et al. | |
| 5,832,455 A | 11/1998 | Hayashi et al. | |
| 5,923,018 A | 7/1999 | Kameda et al. | |
| 6,037,940 A | 3/2000 | Schroeder et al. | |
| 6,052,669 A | 4/2000 | Smith et al. | |

(Continued)

FOREIGN PATENT DOCUMENTS

| | | |
|---|---|---|
| EP | 090971 A2 | 4/1999 |
| EP | 1 065 618 A2 | 1/2001 |

(Continued)

OTHER PUBLICATIONS

U.S. Appl. No. 10/212,556, filed Aug. 5, 2002, Brandt et al.

(Continued)

*Primary Examiner* — Maikhanh Nguyen
(74) *Attorney, Agent, or Firm* — Alexander J Burke (57) ABSTRACT In an embodiment of the present inventions, a work flow process may be generated by decomposing functions of a clinical information system into discrete tasks including an individual task associated with a first pre-configured executable procedure for implementing the individual task and associating a user selectable image element with the pre-configured first executable procedure used in implementing the individual task. In a currently envisioned embodiment, integratable work flow processes according to the present invention may be provided to a vertical application system. It is emphasized that this abstract is provided to comply with the rules requiring an abstract which will allow a searcher or other reader to quickly ascertain the subject matter of the technical disclosure. It is submitted with the understanding that it will not be used to interpret or limit the scope of meaning of the claims.

8 Claims, 11 Drawing Sheets

U.S. PATENT DOCUMENTS

| | | | |
|---|---|---|---|
| 6,064,984 A | | 5/2000 | Ferguson et al. |
| 6,085,184 A | | 7/2000 | Bertrand et al. |
| 6,115,646 A | * | 9/2000 | Fiszman et al. ............... 700/181 |
| 6,151,583 A | * | 11/2000 | Ohmura et al. .............. 705/7.26 |
| 6,208,345 B1 | | 3/2001 | Sheard et al. |
| 6,208,974 B1 | | 3/2001 | Campbell et al. |
| 6,225,998 B1 | | 5/2001 | Okita et al. |
| 6,279,009 B1 | | 8/2001 | Smirnov et al. |
| 6,304,886 B1 | | 10/2001 | Bernardo et al. |
| 6,308,163 B1 | | 10/2001 | Du et al. |
| 6,308,188 B1 | | 10/2001 | Bernardo et al. |
| 6,347,329 B1 | | 2/2002 | Evans |
| 6,430,538 B1 | * | 8/2002 | Bacon et al. ................. 705/7.21 |
| 6,458,080 B1 | * | 10/2002 | Brown et al. ................. 600/300 |
| 6,697,784 B2 | * | 2/2004 | Bacon et al. ................. 705/7.26 |
| 6,728,947 B1 | * | 4/2004 | Bengston ...................... 717/103 |
| 6,966,049 B2 | * | 11/2005 | Lepejian et al. .............. 717/102 |
| 6,970,844 B1 | * | 11/2005 | Bierenbaum .................... 705/39 |
| 7,027,997 B1 | | 4/2006 | Robinson et al. |
| 7,047,535 B2 | * | 5/2006 | Lee et al. ...................... 719/328 |
| 7,184,967 B1 | * | 2/2007 | Mital et al. ................... 705/7.26 |
| 7,240,324 B2 | * | 7/2007 | Casati et al. .................. 717/103 |
| 7,275,039 B2 | * | 9/2007 | Setteducati .................. 705/7.24 |
| 7,296,056 B2 | * | 11/2007 | Yaung ........................... 709/205 |
| 7,428,495 B2 | * | 9/2008 | Dhar et al. ................... 705/7.26 |
| 7,447,644 B2 | | 11/2008 | Brandt et al. |
| 7,653,566 B2 | * | 1/2010 | Kim et al. .................... 705/7.13 |
| 7,937,655 B2 | * | 5/2011 | Teng et al. .................... 715/255 |
| 2001/0032108 A1 | * | 10/2001 | Sieron et al. ....................... 705/7 |
| 2002/0065701 A1 | * | 5/2002 | Kim et al. .......................... 705/9 |
| 2002/0128890 A1 | * | 9/2002 | Dick et al. ......................... 705/8 |
| 2002/0170035 A1 | | 11/2002 | Casati et al. |
| 2003/0023728 A1 | * | 1/2003 | Yaung ........................... 709/226 |
| 2003/0149714 A1 | | 8/2003 | Casati et al. |
| 2003/0158832 A1 | * | 8/2003 | Sijacic et al. ..................... 707/1 |
| 2004/0015841 A1 | * | 1/2004 | Lepejian et al. .............. 717/109 |

FOREIGN PATENT DOCUMENTS

| | | |
|---|---|---|
| WO | WO 99/24927 | 5/1999 |
| WO | WO 00/03344 | 1/2000 |
| WO | WO 0014618 | 3/2000 |

OTHER PUBLICATIONS

Using Domino Workflow www.redbooks.ibm.com International Technical ISupport Organization.

Dewan et al., "Workflow Optimization Through Task Redesign in Business Information Process", IEEE, Jan. 6-9, 1998, pp. 240-252.

Bertino et al., "A Flexible Model Supporting the Specification and Enforcement of Role-based Authorization in Workflow Management Systems", ACM, Nov. 1997, pp. 1-12.

Marazakis et al., "Management of Work Sessions in Dynamic Open Environments", IEEE, Aug. 26-28, 1998, pp. 725-730.

S. Chun, et al., "Dynamic Composition of Workflows for Customized eGovernment Service Delivery," ACM, May 2002, pp. 1-7.

J. Zhao, et al., "Temporal Workflow Management in a Claim Handling System," ACM, Mar. 1999, pp. 187-195.

* cited by examiner

SYSTEM AND USER INTERFACE FOR WORKFLOW AND TASK SCHEDULE CONFIGURATION

PRIORITY

This application is a divisional application of Ser. No. 10/212,556, now U.S. Pat. No. 7,653,873 by S. Brandt et al. filed Aug. 5, 2002 that claims priority through U.S. Provisional Application 60/316,603 filed Aug. 31, 2001 for "A System And User Interface For Supporting Task Schedule Configuration."

BACKGROUND OF THE INVENTION

The present invention relates to work flow management systems in general, and more specifically to work flow engines that may be embedded within a more comprehensive software application, e.g. a healthcare software application system.

A vendor (e.g., a systems integrator, sometimes referred to hereinafter as an "OEM") of software applications amenable to work flow functionality typically needs to supply its end user customer with a means of configuring the customer's work flow supported by the OEM's software system. However, those customers who require such work flow often have to perform substantial work flow configuration processes, including configuring process interface specifications for individual work steps. Thus, an end user customer will also be required to understand not only their own work flow processes but also the intricacies of both interfacing a particular software application to a work flow engine as well as the intricacies of portions of the work flow engine itself.

In traditional systems, an end-user signs on to an information system, performs work tasks, and then signs off. These systems are typically designed to allow the end user to navigate to the functions of choice. Generic work flow engine vendors do not provide requisite functionality for such customers as the generic work flow engine vendors typically do not have knowledge of the work flow relevant capabilities of specific software systems into which their work flow product will be embedded.

Additionally, although work flow engines may be well suited for direct configuration and implementation by end users, work flow engines are not well suited for secondary distribution, e.g. embedding in a second software application environment, in part because they place the entire burden of defining the interaction with the second software application system upon a work flow process designer.

Further, software applications and work flow engines typically provide a single, generic icon to represent a task conducted by an individual, including interfaces to other software systems. The work flow designer typically configures this icon by designating the addressee to whom the task should be assigned. A software application using work flow engines typically assumes that the destination/individual will be able to open a work step, perform the appropriate action, and designate the work step as "completed." Many systems also allow the work flow designer to configure the data entry screen by which the addressee can complete the task. The work flow designer is responsible for configuring this computer system icon with the appropriate parameters needed to execute the desired function in the foreign system.

However, purchasers of a software application, e.g. a specialized or "vertical" system, are buying a solution for a particular market problem. Presumably, individuals in a particular industry will use the system in order to accomplish their own work flow processes as well as other functions afforded by the system.

SUMMARY

As will be understood, a work flow comprises one or more tasks to be accomplished. In an embodiment of the present invention, a user interface that supports user creation of a work flow may be provided by selecting, in response to a user command, a user selectable displayed image element associated with a pre-configured executable procedure to associate the selected displayed image element with a particular task of a work flow. In a preferred embodiment, the particular task comprises a corresponding executable procedure that is useful in implementing the particular task in the work flow, e.g. a particular task to be performed by a predetermined user role. The executable procedure is pre-configured to be associated with (1) a task identifier for the particular task and (2) an executable application for initiating the executable procedure for implementing the particular task and incorporating the particular task into data representing a particular work flow in response to the selection of the displayed image element associated with the particular task.

The user selectable image element may be generated by pre-configuring an executable procedure to be associated with a particular work flow task by associating the executable procedure with (i) a task identifier and (ii) a designated executable application for initiating the executable procedure for implementing the particular task; and associating a user selectable image element with the configured executable procedure to be used in performing a particular work flow task in response to at least one of a user command entered via a displayed user interface and a command from an executable application. These associations are typically accomplished prior to integration of a work flow engine into a second software application system, e.g. a specialized "vertical" software application system.

The present inventions may be utilized in a software application by integrating pre-configured executable procedures into the software application. In a preferred embodiment, for each desired work step, a software application programmer or designer may create a unique work flow executable procedure, e.g. a work flow sub-process, and embed a predetermined set of parameters required to invoke appropriate functionality for the software application within the work flow executable procedure. For example, a software application programmer may configure asynchronous call out and callback, including blocking and timeout logic, required by the executable procedure; expose parameters that must be passed into the executable procedure as public parameters; expose returns that must be passed back to the executable procedure in which the work step will be configured; and/or create a property page for the executable procedure. An image element may be created to represent the executable procedure and then the executable procedure may be secured, thereby making its internal configuration inaccessible to an end user of the software application.

Once properly created, the resultant image element and its associated executable procedure(s) may be included in a library as part of a customized environment for the software application or a work flow engine.

The scope of protection is not limited by the summary of an exemplary embodiment set out above, but is only limited by the claims.

BRIEF DESCRIPTION OF THE DRAWINGS

These and other features, aspects, and advantages of the present invention will become more fully apparent from the following description, appended claims, and accompanying drawings in which:

DETAILED DESCRIPTION OF THE PREFERRED EMBODIMENT

In general, throughout this description, if an item is described as implemented in software, it can equally well be implemented as hardware. Further, as used herein, "end user" and "customer" are understood to comprise a individual user, a group or category of users, a role or characteristic of one or more users, a particular device or system such as a medical device or system, and the like, or a combination thereof.

As used herein, "communication link" comprises data communications pathways, both logical and physical, e.g. interprocess messaging, interprocessor data transmissions, and local and wide area data communications links. "File structure" comprises a data file contained in a transient or permanent storage medium such as RAM or a computer hard drive, a folder or other director structure, a directory, a database, and the like, or a combination thereof, as these terms will be familiar to those of ordinary skill in the computer arts.

Additionally, "executable procedure" is meant to be understood to comprise software that exists within a software application which can be called by another software application or component of a software application, e.g. a work flow process or sub-process. It is understood that as used herein, an "executable procedure" may comprise a work flow sub-process, e.g. a configuration within a work flow engine that will result in task(s) being undertaken by people, computer systems, or a combination thereof such as through a call from a work flow executable procedure to another work flow executable procedure or other machine callable subroutine of executable code.

Further, although one or more components of the present invention will be described herein in object oriented programming terms as will be readily familiar to those of ordinary skill in the object oriented programming arts, the present invention is not limited to nor require object oriented programming.

Figure 1:
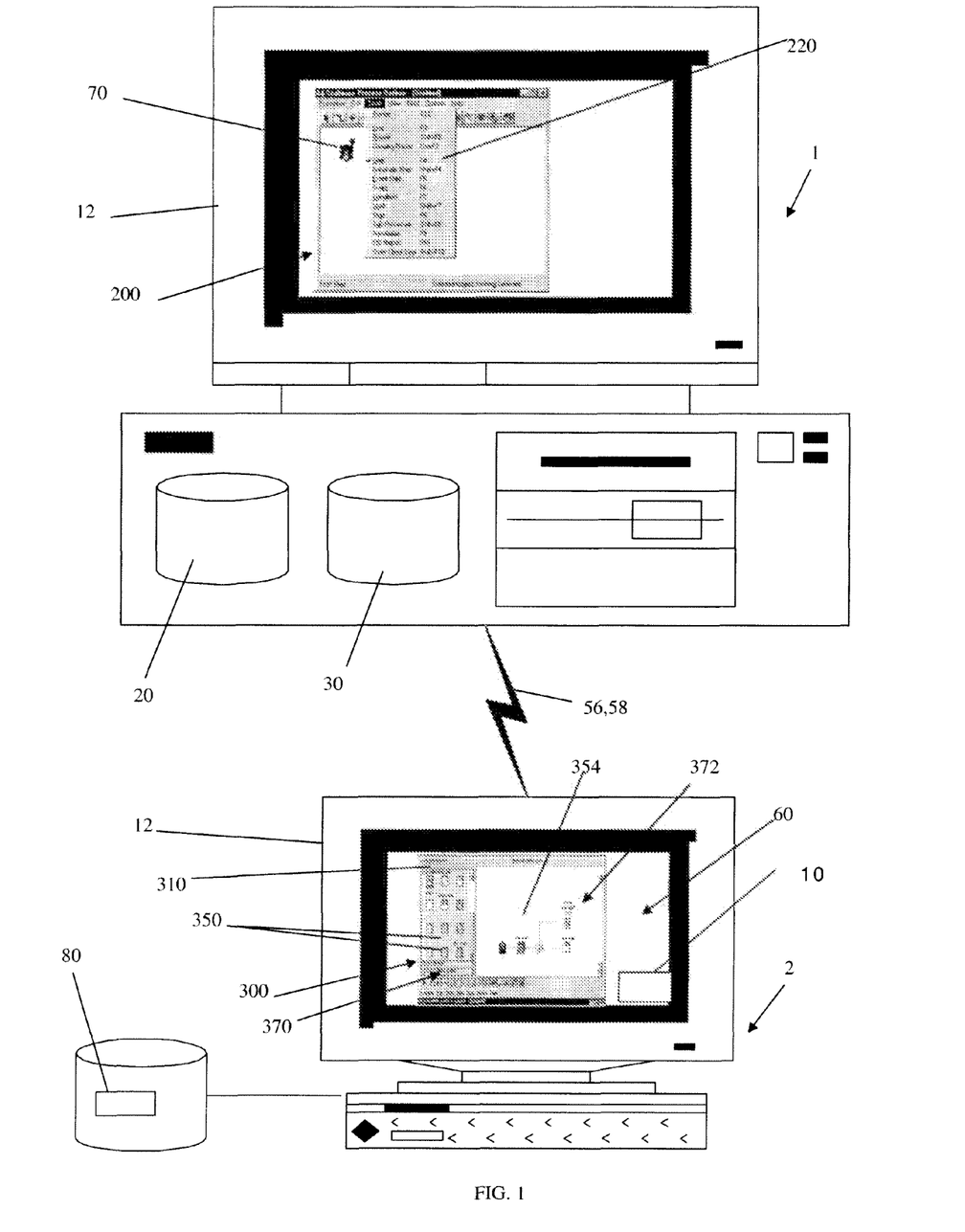
FIG. 1 is a schematic of an exemplary system embodiment.
Figure 5:
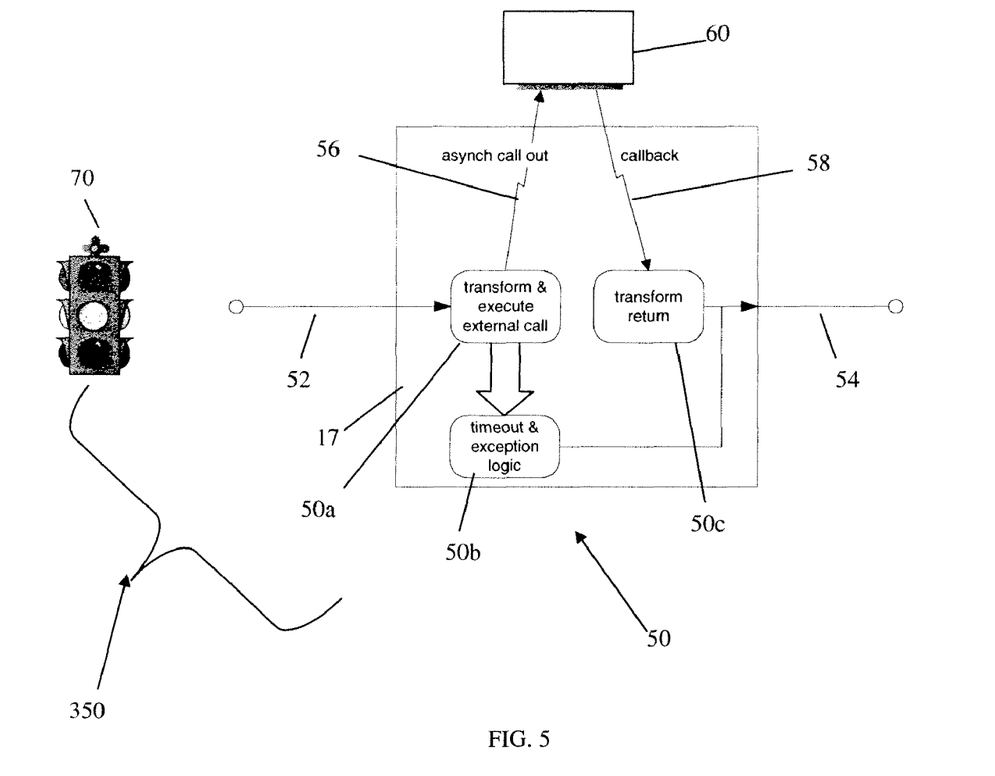
FIG. 5 is a schematic of an exemplary executable procedure and an associated image element of the present invention.

Referring to FIG. 1, a system for a preferred embodiment of the present invention comprises work flow engine 10 which can be embedded or integrated into second software application 60 (sometimes referred to as a "vertical application"); display 12; source 20 of image elements (the image elements generally referred to herein as "350") which can be displayed on display 12; source 30 of work flow executable procedures (the workflow procedures are generally referred herein to by the number "50" and are illustrated in FIG. 5); and work flow process configuration environment 100 (not shown in the figures), which may comprise image element interfaces 200, 300 displayable on display 12.

Work flow engine 10 may be software executable on a variety of computer systems as will be familiar to those of ordinary skill in the work flow software arts. A single computer, e.g. computer 1, may be used to support both configuration and task execution, or a plurality of computers, shown in FIG. 1 as computer 1 and computer 2, may be used, e.g. computer 1 used for configuration and computer 2 used as a workstation executing software application 60.

Additionally, display 12 may be any of a variety of equivalent displays, e.g. a personal computer display, a workstation display, a terminal display, a laptop display, and the like.

Source 20 may be present to allow storage and retrieval of image elements 350. Source 20 or source 30 may also provide for storage and retrieval of executable procedures 50 (FIG. 5). Source 20 and source 30 may comprise one or more physical devices, e.g. a persistent data store such as electronic media, magnetic media, optical media, and the like, or combinations thereof.

Figure 2:
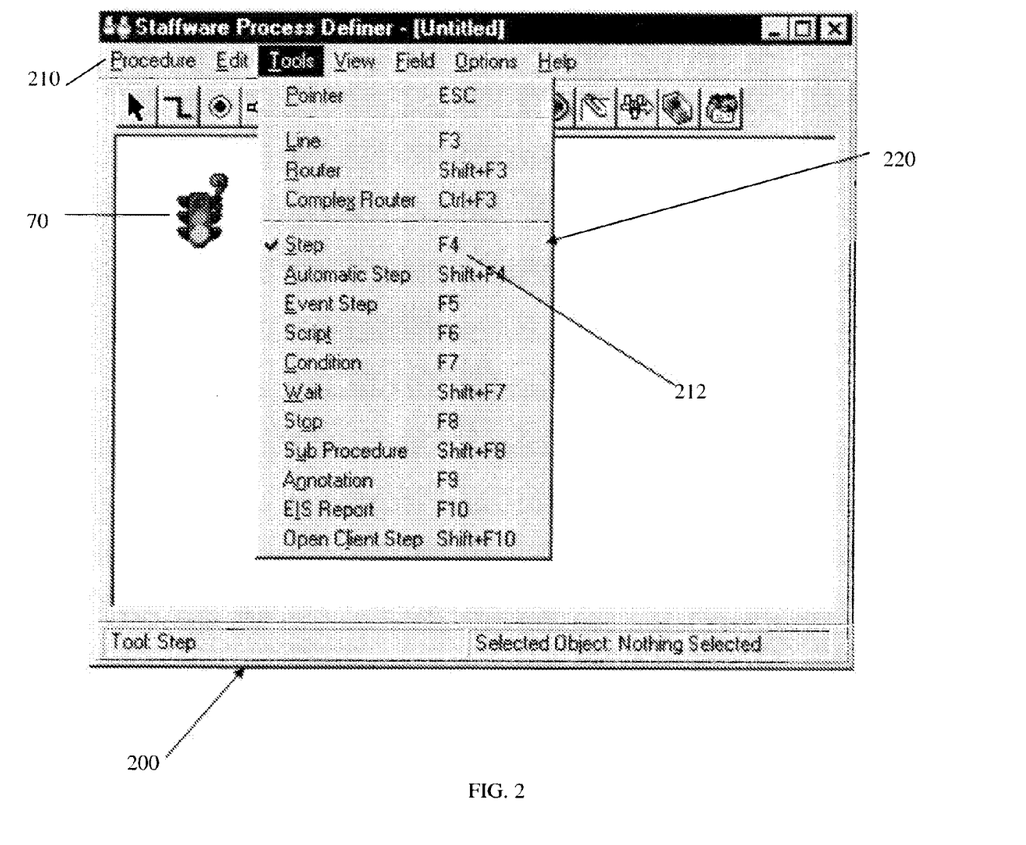
FIG. 2 is a diagrammatic representation of a first exemplary image element interface of the present invention.
Figure 3:
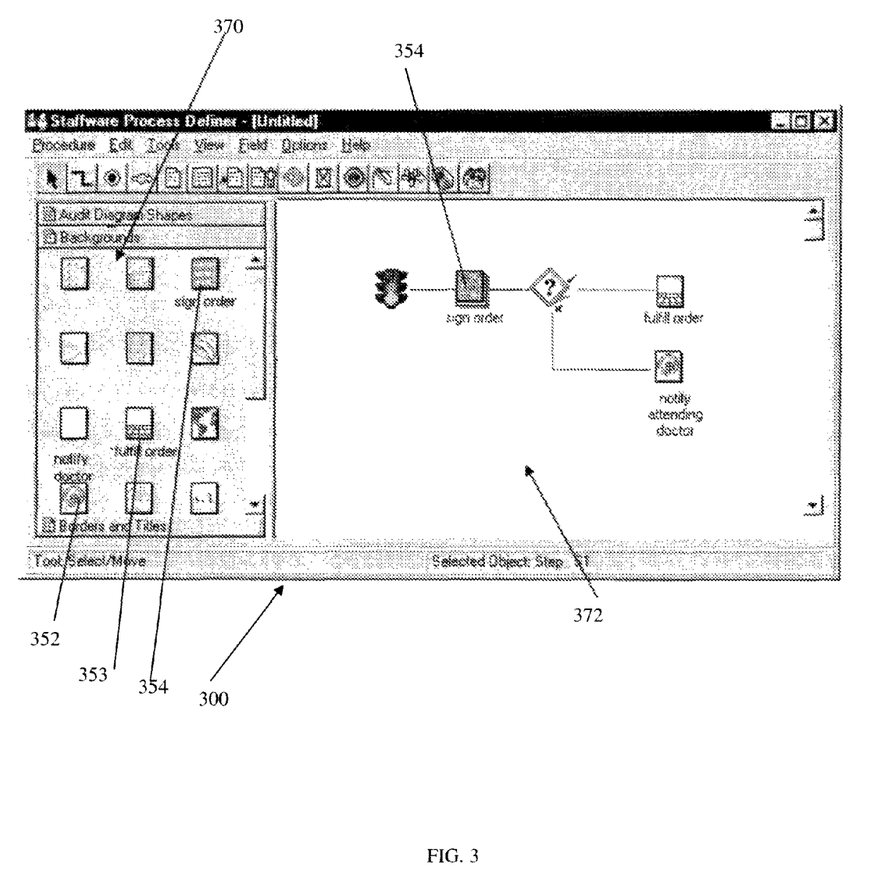
FIG. 3 is a diagrammatic representation of a second exemplary image element interface of the present inventions showing a work flow.

Referring additionally to FIG. 2 and FIG. 3, many work flow engines 10 (FIG. 1) feature a graphical design environment or graphical work flow process configuration environment 100 (not shown in the figures) that allows a work flow process to be defined and/or manipulated, e.g. visually by creating a flowchart of work flow steps to be accomplished (shown at 300 in FIG. 1 and in more detail in FIG. 3). Work flow process configuration environment 100, though not specifically called out as such in the figures, generally includes image element interface such as shown at 200 and 300. Image element interface 200,300 is useful for providing user selection of a predetermined set of work flow functions and a predetermined set of image elements 350. A "tool," as used herein, may be text, icon 70 (FIG. 2), a menu item, a button or selectable screen region, a keyboard entry, or the like, or a combination thereof. For example, to draw a work flow flowchart, a user may either select a tool such as icon 70 (FIG. 2) and place it onto work area 372 (FIG. 1) by dragging-and-dropping, or select a tool such as 212 (FIG. 2) from drop down menu 220 (FIG. 2) accessed via tool bar 210 (FIG. 2) or via a keyboard to be placed onto work area 372.

When work flow engine 10 is executing and reaches a step in the flowchart, e.g. 354 in FIG. 3, work flow engine 10 will put a descriptor of a work process step or task, e.g. a line item, in a work list (not shown in the figures). A user can select that line item in the work list to start the step or task. In a preferred embodiment, selecting a line item in a work list takes the user to a predetermined interface, e.g. information shown on display 12, which may then be used to trigger an automatic program control. Completion of the task using that interface results in a notification to work flow engine 10 of completion of the task, along with any relevant state data. Work flow engine 10 may then proceed with a next step in the work flow process configuration and may use the provided relevant data to determine how to proceed.

In a preferred embodiment, a user interface may comprise two or more separate interfaces, e.g. 200 and 300, to maintain a division between a designer's abilities to interface with both work engine 10 and the separate software application 60, or can be a single interface, e.g. 300.

Figure 4:
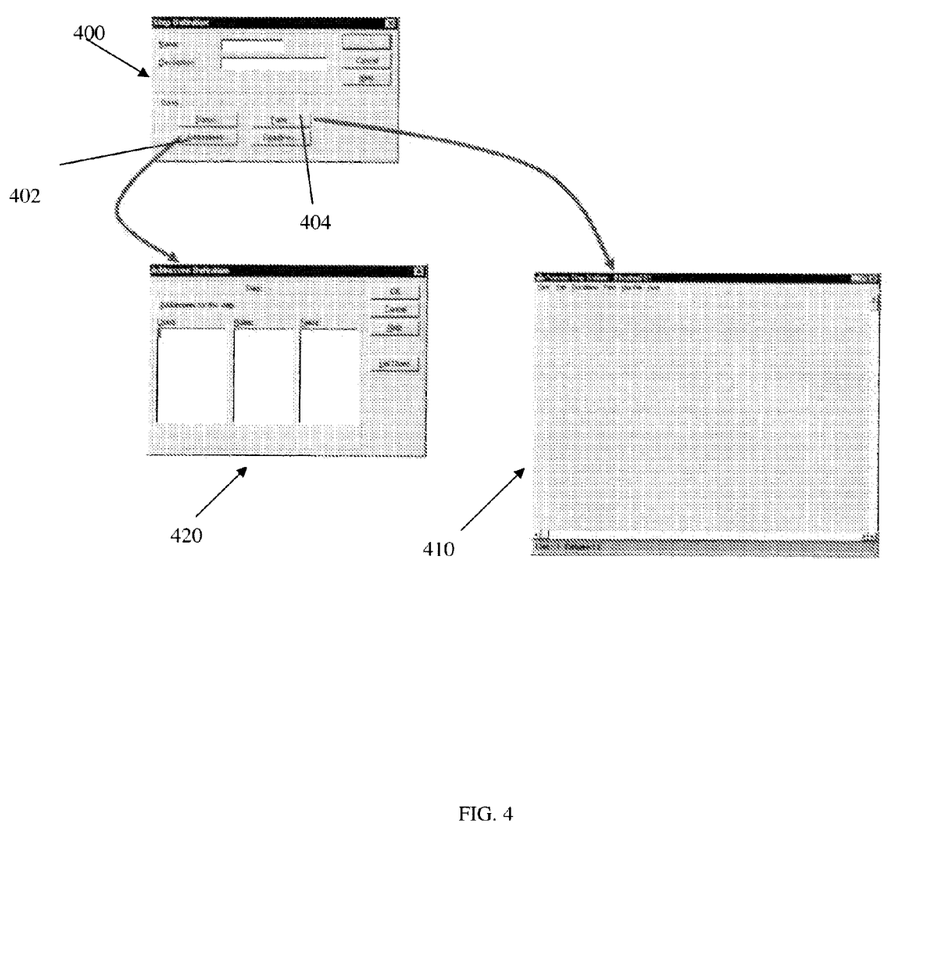
FIG. 4 is a diagrammatic representation of an exemplary set of property pages.

Referring additionally to FIG. 4, when the user selects a tool, e.g. icon 70 (FIG. 1), work engine 10 may then display property page 400 (FIG. 4) to aid in a designer's definition of attributes of the work step associated with the tool, e.g. to further define what a generic work step should do. As shown in FIG. 4, the designer may be able to select multiple configuration items for a desired work step, e.g. click on button 402 to access "Addressee" property page 420 and indicate which user should execute the step or click on button 404 to access form property page 410.

Figure 4A:
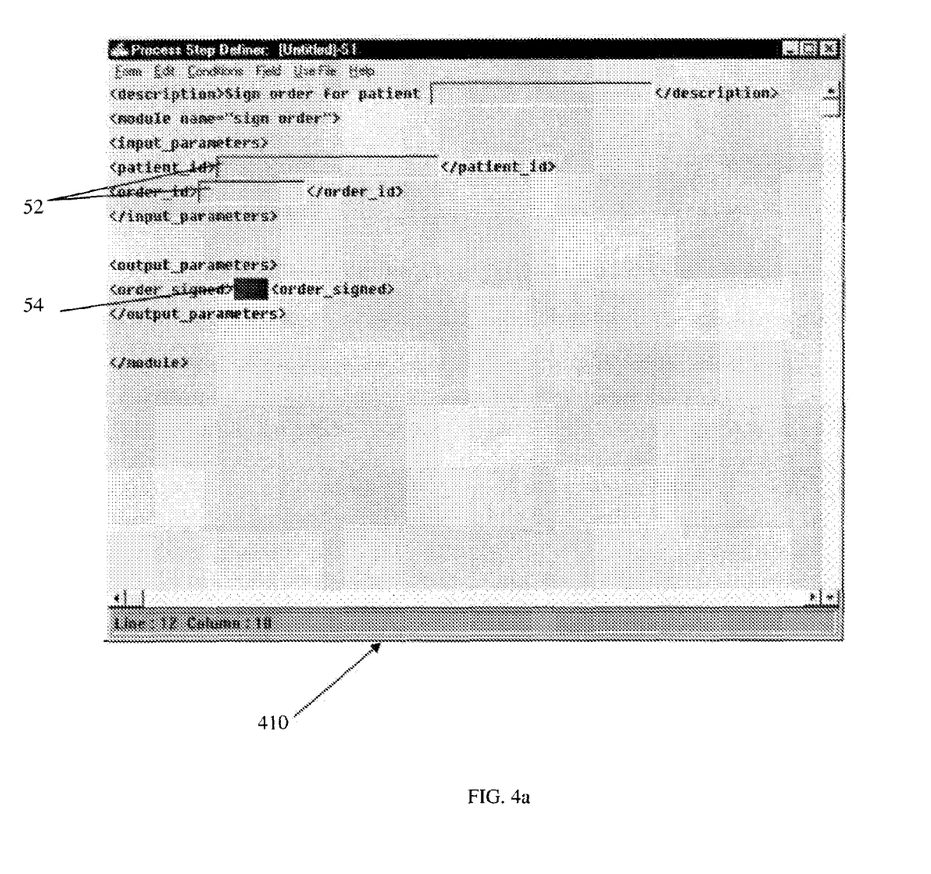
FIG. 4*a* is a diagrammatic representation of an exemplary property page detail.

In a preferred embodiment, form property page 410 (FIG. 4), a more detailed example of which is shown in FIG. 4a, may be used to define how data should be exchanged between a user and work flow engine 10 (FIG. 1), or between a first software application, e.g. work flow engine 10 (FIG. 1), and a second software application, e.g. software application 60 (FIG. 1). As illustrated in FIG. 4a, property pages such as 410 may be used to configure exposed, predetermined sets of public attributes that can be set at design time, including data elements to be exchanged. These data elements may include the name of a function or program, e.g. a function or program to be started when a user selects that item in a work list, or a file name, which may be used to define which function or program should be started to view or edit the file, e.g. through the file's name extension. In the present invention, a software application, e.g. work flow engine 10, can be used as the Addressee.

As also shown in more detail in FIG. 4a, other data elements that can be exchanged may include a name of and a value for input parameters 52 and a name and a value of output parameters 54, including a default value.

Referring additionally to FIG. 5, a work flow comprises a plurality of tasks 17 and a plurality of executable procedures 50. Each task 17 may comprise a function to trigger an event. In a preferred embodiment, image element 350 provides a pre-configured interface to one or more executable procedures 50 of work flow engine 10 (FIG. 1). Image element 350 comprises identifier 51 (not shown in the figures) displayable on display 12, e.g. a prompt element, icon 70, menu item 212 (FIG. 2), text, a symbol, a graphical element, and/or a selectable region of display 12, or the like, or a combination thereof. Image element 350 further comprises executable procedure 50, e.g. functionality to accomplish a programmatic call to work flow engine 10 (FIG. 1) and/or software application 60, to interface to processing occurring within software application 60, and/or to receive a return from software application 60.

As shown in FIG. 5, executable procedure 50 may encapsulate complexities of communicating with a software application, e.g. 60, to accomplish a work step and represent executable procedure 50 to a user as a displayable element, e.g. icon 70 that can be dragged into a work flow design. Complexities of executable procedure 50 may be hidden within executable procedure 50, e.g. transforming input parameters 52 into appropriate system calls for software application 60, making an asynchronous calls to software application 60, passing a callback address, blocking and waiting for callback 58, implementing exception logic to manage timeouts and failures 50b, and, upon receiving callback 58, transforming the results into a form usable by the work flow engine, including transforming callback parameters into work flow relevant data 54.

Executable procedures 50 may be further capable of being embedded within and/or integrated into software application 60 and providing work flow functions to software application 60. Executable procedures 50 may further comprise one or more work flow executable procedure definitions, e.g. 50a, 50b, 50c. Work flow executable procedure definitions 50a, 50b, 50c may comprise a software component associated with a specific task 17 to be performed by software application 60 and/or a user of second software application program 60. Accordingly, executable procedures 50 may be configured to be associated with a unique task 17 of the one or more tasks 17 available within a properly configured work engine 10, software application 60, or a combination thereof.

executable procedures 50 may also comprise input parameter 52 relevant to task 17 and/or output parameter 54 to be generated by performing a particular task 17. Input parameter 52 may also comprise a predetermined input parameter value. Further, in a preferred embodiment, a value of input parameter 52 may comprise an expression which itself comprises a process definition variable for a work flow process in which executable procedure 50 is or will be incorporated. In certain embodiments, input parameter 52 and its predetermined input parameter value may be hidden from the user. Input parameter 52 may further comprise a configurable attribute, e.g. data type, data length, default value, required input parameter, or optional input parameter, or a combination thereof.

Input parameter 52 may also be used to establish one or more parameters required for initiating communication link 56,58 with a second software application program, e.g. a "vertical" software application 60. Communication link 56,58 may be used for providing input parameter 52 to a particular task 17 and/or receiving output parameter 54 provided in response to performance of the particular task 17.

Similarly, output parameter 54 may further comprise a configurable attribute, e.g. data type, data length, or default value, or a combination thereof. For example, as shown in FIG. 4a, input parameter 52 may comprise a configurable address of a source for input parameter 52 and output parameter 54 may comprise an address of a destination for output parameter 54.

Figure 6:
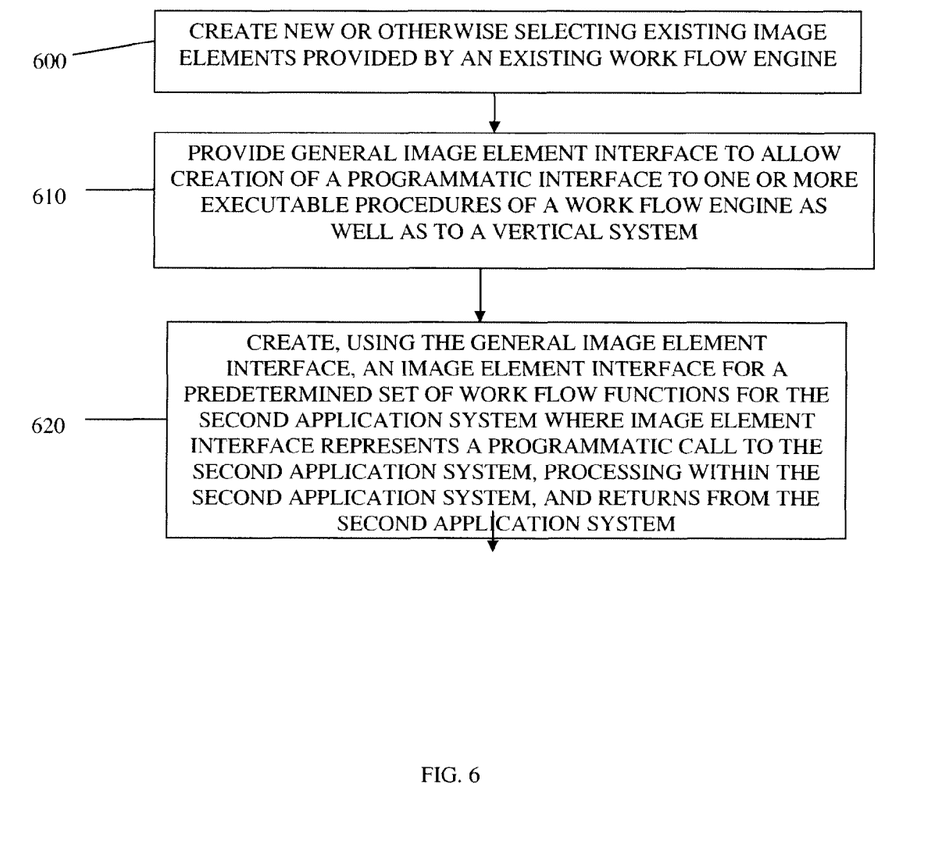
FIG. 6 is a flowchart of an exemplary embodiment of user interface creation.

In the operation of an exemplary embodiment, referring additionally to FIG. 6, work flow engine 10 (FIG. 1) may be integrated into a second application system, e.g. software application 60 (FIG. 1), to provide work flow functionality. It is often desirable to have an individual executable procedure 50 (FIG. 5) correspond to a unique task 17 (FIG. 5). Image elements 350 (FIG. 1) may be integrated into a second application system, e.g. software application 60, by creating, step 600, new or otherwise selecting existing image elements 350 provided by an existing work flow engine 10. A general image element interface, e.g. 200 shown in FIG. 2, is then provided, step 610, to allow creation of a programmatic interface to one or more executable procedures 50 of work flow engine 10 as well as to software application 60, e.g. to allow processing within software application 60 and returns from software application 60. Using the general image element interface, a user such as a designer then creates, at step 620, image element interface 350 for a predetermined set of work flow functions for a second software application system, e.g. software application 60, where image element interface 350 represents a programmatic call to software application 60, processing within software application 60, and returns from software application 60.

Figure 7:
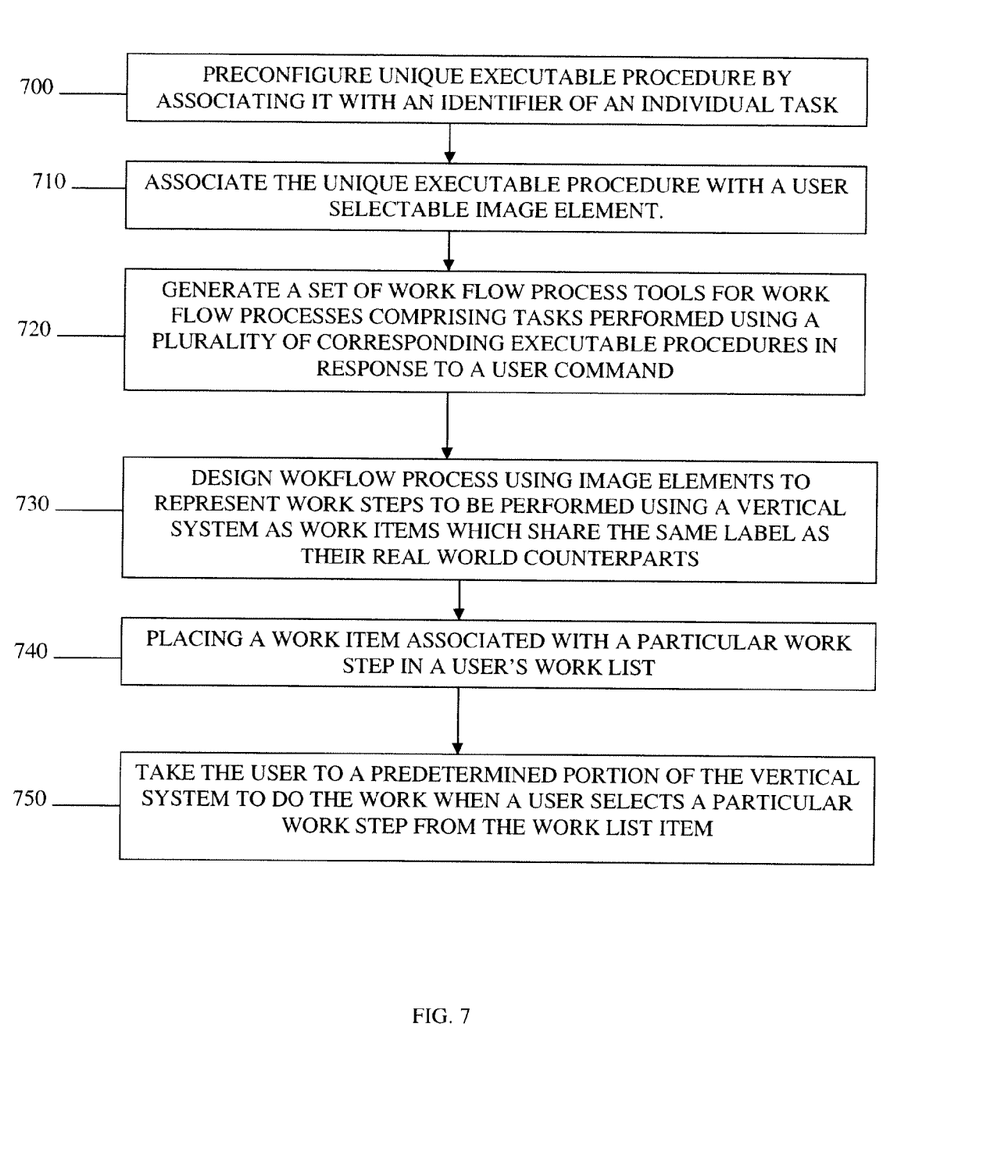
FIG. 7 is a flowchart of a portion a method of an exemplary embodiment.

Referring now to FIG. 7, a set of work flow process tools may be generated, e.g. by a work flow software manufacturer, for work flow processes comprising tasks 17 performed using a plurality of corresponding executable procedures 50 in response to a user command, e.g. dragging-and-dropping icon 70 (FIG. 2) onto work area 372 (FIG. 2). The unique executable procedure 50 is itself pre-configured, step 700, by being associated with identifier 51 of the individual task 17, e.g. a text string describing the task or a recognizable iconographic representation of a task. The unique executable procedure 50 is further associated, step 710, with a user selectable image element 350.

Accordingly, the present invention provides for decomposed interfaces into a work flow where the decomposed interface represents a collection of configurable, discrete tasks 17 (FIG. 5). These discrete tasks 17 are presented by image elements 350 (FIG. 1) which can comprise work flow icons 70 (FIG. 1), work list items, and programmatically callable interfaces, e.g. executable procedure 50 (FIG. 5). A designer of a software application 60 (FIG. 1), e.g. an OEM, may then perform a predetermined amount of pre-configuration of these image elements 350, e.g. step 720. In this manner, instead of being provided with a single icon 70 and being required to understand the intricacies of either software application 60 or work flow engine 10 (FIG. 1) or both, an end-user of software application 60 utilizes natural work steps which are required to configure their specific work flow process. The designer may accordingly use the present invention to represent work steps to be performed using software application 60 as work items which share the same label, e.g. identifier 51, as their real world counterparts, step 730.

For example, in a traditional clinical information system, an end user, typically a clinician, signs on to a clinical information system, performs work tasks 17 (FIG. 5), and then signs off. These systems are typically designed to allow the clinician to navigate to functions of choice.

In a clinical information system embodiment of the present invention, clinical information system 60 (FIG. 1) is presented as a collection of task-oriented image elements 350 (FIG. 1) associated with decomposed functions which can be used to permit clinicians to accomplish discrete tasks 17 (FIG. 5). Functions of clinical information system 60 are decomposed into discrete tasks 17 where each discrete task 17 may be associated with a unique executable procedure 50 (FIG. 1) for implementing the individual task 17. These functions of clinical information system 60 may include processing an order associated with medical treatment of a patient, processing results of a test performed for a patient, documenting clinical findings associated with a patient, scheduling a service to be performed for a patient, managing resources associated with treatment of a patient, and/or managing personnel associated with treatment of a patient, or the like, or combinations thereof.

In this manner, a targeted software application 60 (FIG. 1) is decomposed into a plurality of discrete tasks 17 (FIG. 5), perhaps numbering in the hundreds. Each such discrete task 17 is then represented in an associated work flow design environment 100 (not shown in the figures) as an image element 350, e.g. using icon 70 (FIG. 2). Configuration tools, as described more fully herein, may be provided to aid configuration.

A work flow process can then be designed using image elements 350 (FIG. 1). When a particular work step, i.e. one represented by image element 350, is executed, the work item associated with that particular work step is placed in a user's work list, step 740. When the user selects the work list item, e.g. from the work list, software application 60 (FIG. 1) can take the user, step 750, to a predetermined portion of software application 60 to do the work, e.g. a specific displayed screen associated with that discrete task 17 (FIG. 5).

Figure 8:
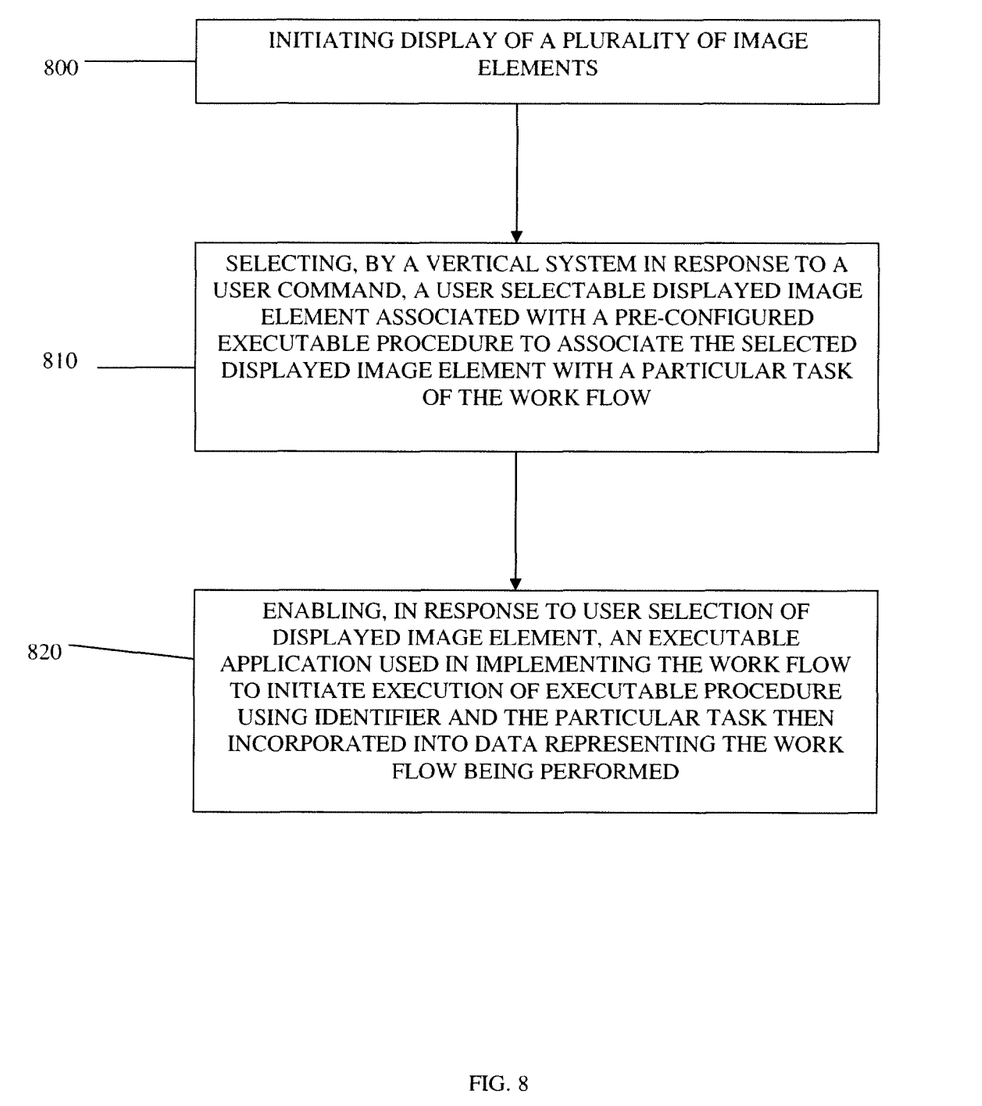
FIG. 8 is a flowchart of an exemplary embodiment of creation of a work flow.

Referring now to FIG. 8, in a preferred embodiment a user interface supporting user creation of a work flow, e.g. including 200 and 300 in FIG. 1, may be provided by initiating, step 800, display of a plurality of image elements 350 (FIG. 1). Software application 60 (FIG. 1) then selects, at step 810 in response to a user command, a user selectable displayed image element 350 (FIG. 1) associated with a pre-configured executable procedure 50 (FIG. 5) to associate the selected displayed image element 350 with a particular task 17 (FIG. 5) of the work flow. As noted herein, executable procedure 50 is pre-configured to be associated with task identifier 51 for the particular task 17 and an executable procedure for implementing the particular task 17, e.g. a function in work flow engine 10 (FIG. 1) or software application 60. For these work flows, an individual task 17 comprises one or more corresponding executable procedures 50. That particular task 17 is then incorporated into data representing a particular work flow in response to the selection of the displayed image element 350 associated with the particular task 17. Accordingly, in response to user selection of displayed image element 350, an executable application used in implementing the work flow to initiate execution of executable procedure 50 using identifier 51 is enabled, step 820, and the particular task 17 is then incorporated into data representing the work flow being performed.

For example, in a clinical information system embodiment that incorporates the present invention, the particular task 17 (FIG. 5) is selectable from a set of tasks 17 derived by decomposing functions of the clinical information system into discrete tasks 17 that include the individual task 17 desired. A desired executable procedure 50 is pre-configured by being associated with identifier 51, e.g. one that relates to the specific task.

Although this example has been presented in terms of a clinical information system, the present invention is applicable to and may be integrated into any of a number of software application 60 (FIG. 1) needing to utilize work flow technology. The designer of software application 60 provides interfaces and functions for the accomplishment of real world tasks 17 (FIG. 5). By building a solution which exposes discrete work steps as configurable items, and by building a user-friendly, graphical design environment which represents each exposed work step as image element 350 (FIG. 1) and minimizes the work required by the designer to incorporate that step within a process, it is possible to create reengineered work flow processes that can be successfully executed by a partnership between software application 60 and work flow engine 10.

Figure 9:
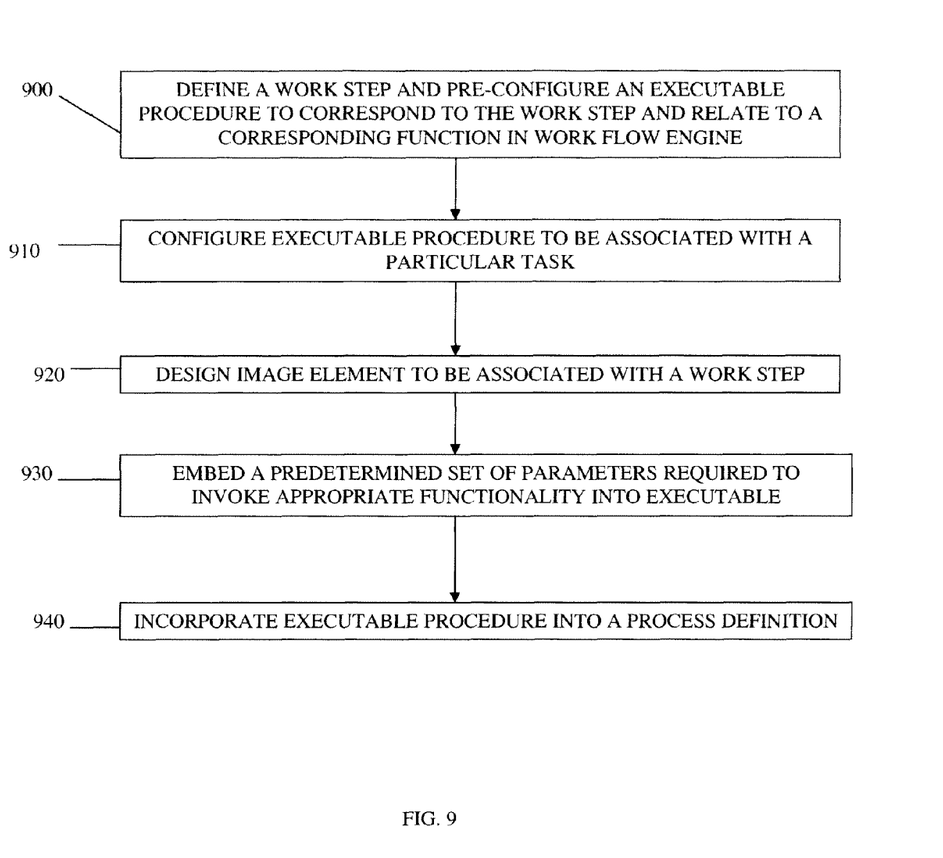
FIG. 9 is a flowchart of an exemplary embodiment of the present invention.

Referring now to FIG. 9, in general a designer defines, at step 900, a work step and then pre-configures executable procedure 50 (FIG. 5) to correspond to the work step and relate to a corresponding function in work flow engine 10 (FIG. 1). In a preferred embodiment, a designer implements unique work flow functionality as executable procedures 50 for each desired work step in a work flow system. It is understood that a plurality of such work steps may be present, numbering into the tens or hundreds of steps depending on the environment into which software application 60 (FIG. 1) is to be placed. When operational, input parameters 52 (FIG. 5) may be passed to executable procedure 50 representing the work flow step function, and work flow step output may be passed via output parameters 54 (FIG. 5).

After the designer has defined the work step, to further generate the user selectable image element 350 (FIG. 1) for executable procedure 50 (FIG. 5), executable procedure 50 may be configured, step 910, to be associated with a particular task 17 (FIG. 5). In a preferred mode, this may be accomplished by associating executable procedure 50 with task identifier 51 and with a designated executable application function, e.g. 50a,50b,50c (FIG. 5). Executable application function 50a,50b,50c may be used to initiate executable procedure 50 when implementing particular task 17, e.g. a particular task 17 to be performed by a predetermined user role.

The designer may design image element 350 (FIG. 5) to be associated with a work step, step 920, by taking an initial, generic work step image element 350 (FIG. 1) and configuring it to be associated with a specific, unique work step that represents a unique task 17 (FIG. 5). The designer may assign image element 350 to the work step and associate image element 350 with task identifier 51, e.g. icon 70 (FIG. 1), text, or list of step or function names, or the like, or a combination thereof. In a preferred embodiment, icons 70 are selected from an icon library.

Once executable procedure 50 (FIG. 5) is created, a predetermined set of parameters required to invoke appropriate functionality, e.g. of software application 60 (FIG. 1), within the work flow executable procedures are embedded, step 930, into executable procedure 50. For example, input parameter 52 (FIG. 5) may be established to aid in initiating communication link 56,58 (FIG. 1) with an application program, e.g. work engine 10 (FIG. 1) or software application 60 (FIG. 1). In a preferred embodiment, communication may then be accomplished by establishing at least one of an input parameter 52 (FIG. 5) and/or an output parameter 54 (FIG. 5) for executable procedure 50; initiating a communication link 56,58 with another application element, e.g. work engine 10 or software application 60; and using communication link 56,58 for providing input parameter 52 to a particular task 17 and/or receiving output parameter 54 provided in response to performance of a particular task 17.

Once defined, executable procedure 50 (FIG. 5) may be incorporated into a process definition, step 940. In certain situations it may be desirable to define a value of parameter 52,54 (FIG. 5), e.g. a variable of the process definition in which executable procedure 50 is incorporated, as an expression comprising one or more output parameters 54 of executable procedure 50. In a preferred embodiment, the value of the process definition variable may be automatically assigned to parameter 52,54 of executable procedure 50 that has the same name as the process definition variable. A process definition variable may also be automatically created and given the name of parameter 52,54 of executable procedure 50.

Additionally, call out 56 (FIG. 5) and callback 58 (FIG. 5) required by work flow executable procedures, which may be asynchronous and may include blocking and timeout logic, may be configured; parameters that must be passed into the work flow executable procedures may be exposed as public parameters; and returns that must be passed back to executable procedure 50 in which the work step will be configured may be exposed. Extensible markup language (XML), which may be expected by second software application 60 (FIG. 1), may be used when executable procedure 50 passes data to and receives data from software application 60.

Image element 350 (FIG. 1) may be selected from an existing set of image elements 350 or created anew. Once created and defined, a work flow definition tool reflecting the present invention, including the pre-configured image elements 350, may then be provided to others such as designers of software applications 60 (FIG. 1) and/or end users of software applications 60. The process of pre-configuring image elements 350 can therefore be performed independently from initiating display of the pre-configuring image elements 350 on a display device and incorporating tasks 17 (FIG. 5) corresponding to a displayed pre-configured image element 350 into a work flow process definition.

Property page 400 (FIG. 4) for executable procedure 50 (FIG. 5) may be created and used when configuring and/or tailoring one or more properties of a work flow as represented by executable procedure 50. The end user may be allowed to configure property pages 400, e.g. specify that one or more parameters are to be set at runtime.

Accordingly, the designer may create an image element 350 (FIG. 1) for each work flow function desired, e.g. if there are five hundred functions, the designer may create five hundred image elements 350, each corresponding to a decomposed work step pre-configured according to the present invention. Once associated with the configured executable procedure 50 (FIG. 5), user selectable image element 350 can be used in performing a particular task 17 (FIG. 5) in response to at least one of a user command entered via displayed user interface 200,300 (FIG. 1), a command from an executable application, or the like, or a combination thereof.

For example, referring back to FIG. 3, once displayed, a user can browse or otherwise see which image elements 350 are available, such as at 370, indicating which of a predetermined number of pre-configured executable procedure 50 are available. As shown in the example in FIG. 3, a user can scroll image elements 350 in window 370 and see a display of task identifiers 51 for each image element 350 available (in FIG. 3, task identifiers 51 comprise icons 352, 353, and 354 and their associated text). The user is then allowed to retrieve a desired pre-configured executable procedure 50 from available executable procedure 50, e.g. a library, by selecting one or more of the displayed image elements 350. The end user may then create a work flow by selecting from a group of image elements 350 (such as shown generally in FIG. 3 grouped in area 370), e.g. by drag-and-drop, mouse click, keyboard, or the like, or combinations thereof.

In an exemplary healthcare work flow software application 60 (FIG. 1), illustrated in FIG. 3, three tasks 17 (FIG. 5) may be desired: sign an order for medication, obtain the desired medication, and notify the doctor that the order is not signed. For this exemplary "Sign Order" function, a designer can create a "Sign Order" work step, specify that the "Addressee" property is a desired value, e.g. the name or identifier of a software application, and specify the content of property page 420 (FIG. 4). This "Sign Order" work step may then be associated with an icon 70 (FIG. 2) to create image element 354 uniquely associated with a "Sign Order" task 17.

Figure 10:
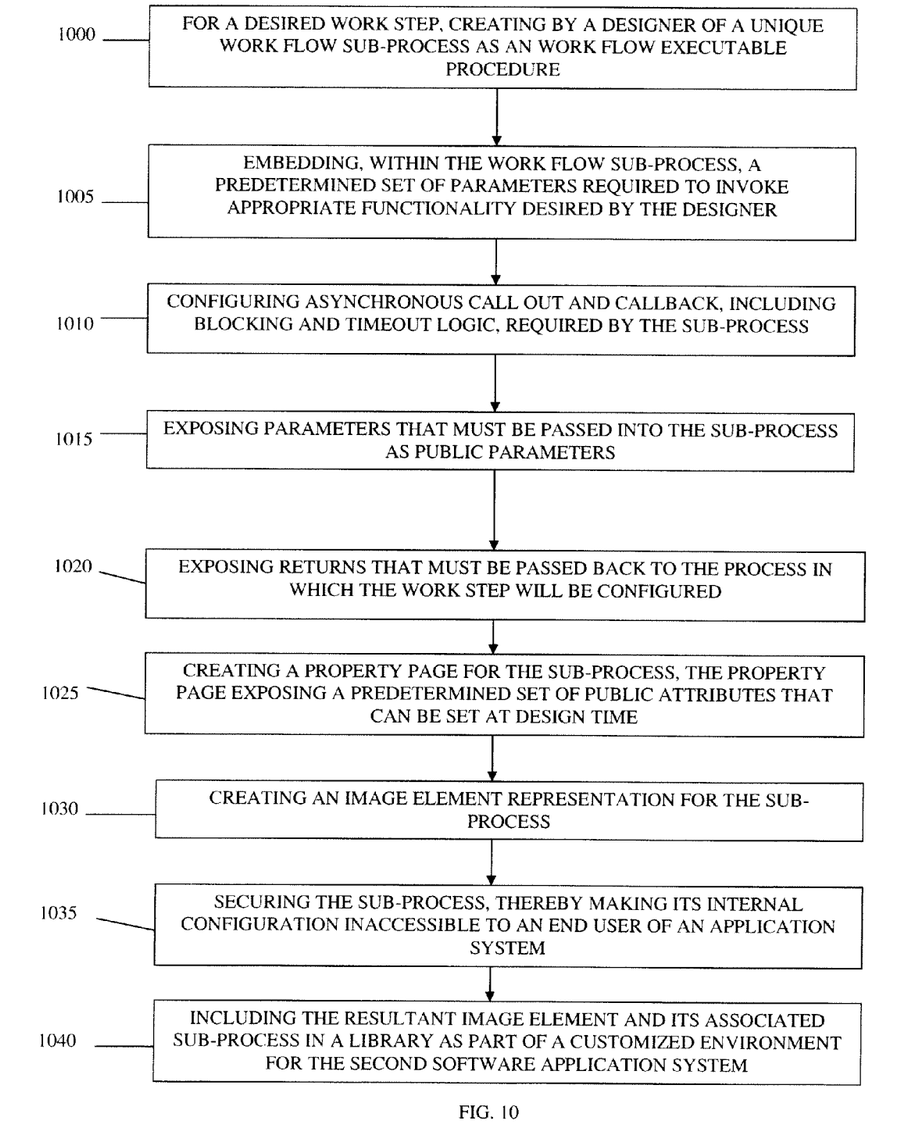
FIG. 10 is a flowchart of an exemplary embodiment of embedding the present invention into a software application.

Referring now to FIG. 10, a flowchart of a method of a preferred embodiment, in the present invention, for every desired function in a work flow, a user can create or otherwise define a work flow executable procedure 50a,50b,50c (FIG. 5) related to a work flow step, step 1000, as an executable procedure 50 (FIG. 5) in work flow engine 10 (FIG. 1), e.g. by using image element 350 (FIG. 1), and specify various attributes for that work step or executable procedure 50, e.g. via content on property page 410 (FIG. 4a) associated with that work step. Once created or generated, a predetermined set of parameters 52,54 (FIG. 5) required to invoke appropriate functionality desired by the designer are embedded, step 1005, within work flow executable procedure 50a,50b,50c (FIG. 5). As required by executable procedure 50a,50b,50c, call out 56 (FIG. 5) and callback 58 (FIG. 5), which can be asynchronous, are configured, step 1010, which may include blocking and timeout logic. Parameters 52,54 (FIG. 5) may then be exposed, steps 1015 and 1020, e.g. those that must be passed to executable procedure 50a,50b,50c as public parameters and those that must be passed back to the process in which the work step will be configured such as to work flow engine 10 (FIG. 1) or software application 60 (FIG. 1). Property page 420 (FIG. 4) may then be created, step 1025, for executable procedure 50a,50b,50c, where property page 420 exposes a predetermined set of public attributes that can be set at design time. Image element representation 350 may then be created, step 1030, for the executable procedure, e.g. icon 70 in FIG. 2. If desired, executable process 50, e.g. 50*a*,50*b*,50*c*, may be secured, step 1035, such as by making its internal configuration inaccessible to an end user of an application system. Once completed and, if desired, secured, the resultant image element 350 and its associated executable procedure 50 may be incorporated in a library, step 1040, as part of a customized environment for a second software application system, e.g. software application 60.

Image elements 350 (FIG. 1) may be retrievably stored such as by installing them in a database or library or file structure, for later retrieval and use. The library may be a manipulatable library such as will be familiar to those of ordinary skill in the programming arts, a file and/or folder structure, or the like, or a combination thereof.

Once executable procedure 50 (FIG. 5) has been configured and stored, e.g. in a library, it may be integrated into another software application, e.g. software application 60 (FIG. 1). As part of the pre-configuration, a designer may also specify which parameters 52,54 (FIG. 5) are public and which are hidden, including a pre-configured flowchart for executable procedure 50. When integrating image element 350 (FIG. 1) into software application 60, a developer of software application 60 may then only get access to image element 350 and its public parameters 52,54.

Typically, access to the library is read-only. Further, an end user may be allowed access to the library from a work flow user interface, e.g. 300 in FIG. 3. For example, the user may only be allowed to retrieve a desired pre-configured executable procedure 50 (FIG. 5) from the library such as by dragging and dropping an icon from icon region 370 (FIG. 1) onto work area 372 (FIG. 1) to create a work flow design. Software application 60 (FIG. 1) may also initiate display of a menu indicating a task schedule, e.g. a task schedule that is associated with a role performed by an individual such as the user.

As described above, executable procedure 50 (FIG. 5) is pre-configured to be associated with task identifier 51 and an executable application for initiating executable procedure 50 when implementing a particular task 17 (FIG. 5). Software application 60 (FIG. 1) then incorporates a particular task 17 into a particular work flow in response to the user's selection of displayed image element 350 (FIG. 1) that is associated with particular task 17. Software application 60, in response to the user command, selects image element 350 which is associated with pre-configured executable procedure 50 to associate the selected displayed image element 50 with a particular task 17 of the work flow.

Users of software application 60 (FIG. 1) may then be prompted to perform a particular task 17 (FIG. 5). As software application 60 executes, record 80 (FIG. 1) may then be created to aid in indicating user progress in accomplishing the particular task 17. For example, record 80 may be created for use in identifying input parameter 52 (FIG. 5) and output parameter 54 (FIG. 5). Record 80 may then be used by executable procedure 50 in acquiring input parameter 52 and exporting output parameter 54. For example, record 80 may be used for storing a parameter for use in performing a particular task 17 where the parameter is useful for automatically establishing communication link 56,58 (FIG. 1) when acquiring input parameter 52 or exporting output parameter 54 in response to initiation of performance of the particular task 17. Data representing a particular work flow may comprise a flowchart, a script, or the like, or a combination thereof.

Referring generally to FIG. 1, in a currently envisioned embodiment, program code may be used in addition to or in place of image elements 350, e.g. implementation of functionality of work flow engine 10 may use a script with or instead of a iconographic flowchart to specify in which order the work should flow. For example, the following script may be present in software application 60:

```
PROCESS A
   STEP(SYSTEM1, SIGN_ORDER, INPUT_PARAMETER1,
OUTPUT_PARAMETER1)
   IF OUTPUT_PARAMETER1="YES" THEN
   STEP(SYSTEM1, OBTAIN_MEDICATION,
   INPUT_PARAMETER1)
   ELSE
   STEP(SYSTEM1, NOTIFY_DOCTOR, INPUT_PARAMETER1,
INPUT_PARAMETER3)
   ENDIF
END PROCESS
```

This script could be replaced with a new procedure according to the present invention that corresponds to a specific function, in software application 60 named "SOARIAN," by use of the following script:

```
PROCESS SIGN_ORDER INPUT1
   STEP("SOARIAN","SIGN ORDER",INPUT1, OUTPUT1)
END PROCESS
PROCESS OBTAIN_MEDICATION INPUT1, OUTPUT1
   STEP("SOARIAN","OBTAIN_MEDICATION",INPUT1, OUTPUT1)
END PROCESS
PROCESS NOTIFY_DOCTOR INPUT1, OUTPUT1
   STEP("SOARIAN","NOTIFY DOCTOR",INPUT1, OUTPUT1)
END PROCESS
```

As the user writes the script, the user can select procedures 50 (FIG. 5) from a list of image elements 350, e.g. using text or icons 70. An exemplary resulting script may then read:

```
PROCESS A
   SIGN_ORDER(INPUT_PARAMETER1, OUTPUT_PARAMETER1)
   IF OUTPUT_PARAMETER1="YES" THEN
   OBTAIN_ORDER(INPUT_PARAMETER1)
   ELSE
   NOTIFY_DOCTOR(INPUT_PARAMETER1,
   INPUT_PARAMETER3)
   ENDIF
END PROCESS
```

Each executable procedure 50 (FIG. 5) in the exemplary script above corresponds to a function or module in work flow engine 10. The user of work flow engine 10 does not have to write these executable procedure 50 and does not even have to know how these executable procedure 50 work. To instruct work flow engine 10 to get it to do something specific, the user simply uses the appropriate predefined or pre-configured executable procedure 50. One benefit of the present invention is that if a vendor changes the implementation of work flow engine 10, the vendor would also change the definitions of the pre-configured executable procedure 50 but the user of work flow engine 10, e.g. the end user of software application 60, would not know the difference.

It will be understood that various changes in the details, materials, and arrangements of the parts which have been described and illustrated above in order to explain the nature of this invention may be made by those skilled in the art without departing from the principle and scope of the invention as recited in the following claims.

The invention claimed is:

1. A method of providing a pre-configured work flow executable procedure associated with a workflow step for operation with a software executable application associated with a workflow process including a plurality of workflow steps, comprising of:
in response to user command,
associating with an executable procedure of a work step, a predetermined set of parameters required to invoke functions of said executable procedure;
exposing input parameters to be provided to said executable procedure by a workflow process as public parameters;
exposing output parameters of said executable procedure to be returned to said workflow process incorporating said work step;
providing a property of said executable procedure used to expose a predetermined set of user selectable public parameter attributes for use by a workflow process;
creating an image element representing said executable procedure;
including the created image element and its associated executable procedure in at least one library usable for customizing said workflow process;
enabling a user to select parameters and add said executable procedure to said workflow process; and
making an internal configuration of said executable procedure inaccessible to an end user of an application system.

2. The method according to claim 1, further comprising the step of:
providing said user configurable workflow work steps comprising decomposed functions of a clinical information system.

3. The method according to claim 1, wherein said workflow process is implemented using said software executable application and further comprising the steps of:
enabling a user of said software executable application to add said executable procedure to said software executable application by dragging said created image element into a representation of said workflow process; and
enabling said user of said software executable application to select said user selectable public parameter attributes.

4. The method according to claim 1, wherein:
said image element is at least one of a graphical element and a text element.

5. The method according to claim 1, further comprising the steps of:
incorporating said executable procedure into a process definition; and
deriving a value of a variable of the process definition using an expression processing one or more of said output parameters.

6. The method according to claim 1, wherein:
said functions of said executable procedure comprise functions of said workflow process for performance by healthcare personnel.

7. A computer program embodied within a non-transitory computer-readable medium created using the steps of the method of claim 1.

8. A system including at least one computer for providing a pre-configured work flow executable procedure associated with a workflow step for operation with a software executable application associated with a workflow process including a plurality of workflow steps, comprising:
a workflow engine for in response to user command,
associating with an executable procedure of a work step, a predetermined set of parameters required to invoke functions of said executable procedure;
exposing input parameters to be provided to said executable procedure by a workflow process as public parameters;
exposing output parameters of said executable procedure to be returned to said workflow process incorporating said work step;
providing a property of said executable procedure used to expose a predetermined set of user selectable public parameter attributes for use by a workflow process;
providing user configurable workflow work steps represented by image elements:
creating an image element representing said executable procedure;
including the created image element and its associated executable procedure in at least one library usable for customizing said workflow process;
enabling a user to select parameters and add said executable procedure to said workflow process; and
making an internal configuration of said executable procedure inaccessible to an end user of an application system.

* * * * *